(12) United States Patent
El Zoghbi et al.

(10) Patent No.: US 10,966,834 B2
(45) Date of Patent: Apr. 6, 2021

(54) BREAK OFF SPACER CLIP FOR TROCHANTERIC FEMORAL NAIL TELESCOPING HEAD ELEMENT

(71) Applicant: DePuy Synthes Products, Inc., Raynham, MA (US)

(72) Inventors: Gaser El Zoghbi, Solothurn (CH); Rhett Rapier, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 554 days.

(21) Appl. No.: 15/879,936

(22) Filed: Jan. 25, 2018

(65) Prior Publication Data

US 2019/0224013 A1 Jul. 25, 2019

(51) Int. Cl.
*A61F 2/30* (2006.01)
*A61F 2/46* (2006.01)
(Continued)

(52) U.S. Cl.
CPC ........ *A61F 2/30739* (2013.01); *A61B 17/742* (2013.01); *A61B 17/8872* (2013.01); *A61F 2/4607* (2013.01); *A61F 2/4612* (2013.01); *A61B 17/1664* (2013.01); *A61B 17/1746* (2013.01); *A61B 17/8685* (2013.01); *A61B 2017/681* (2013.01); *A61B 2090/037* (2016.02); *A61F 2/30907* (2013.01); *A61F 2/36* (2013.01); *Y10T 24/3982* (2015.01); *Y10T 24/4501* (2015.01); *Y10T 24/45178* (2015.01); *Y10T 24/45461* (2015.01)

(58) Field of Classification Search
CPC .. A61F 2/30739; A61F 2/4607; A61F 2/4612; A61F 2/30907; A61F 2/36; A61B 17/742; A61B 17/8872; A61B 17/1664; A61B 17/1746; A61B 17/8685; A61B 17/684; A61B 2090/037; Y10T 24/45178; Y10T 24/45461; Y10T 24/45534; Y10T 24/4501; Y10T 24/3982; A01K 27/005; A44B 11/2588
USPC ......... 606/80; 81/44, 13, 451, 452, 454, 458
See application file for complete search history.

(56) References Cited

U.S. PATENT DOCUMENTS

| 1,977,323 A * | 10/1934 | Morgan | ................ B25B 23/101 |
| | | | 81/458 |
| 3,730,237 A * | 5/1973 | Hanzlik | ................ B25B 23/101 |
| | | | 81/456 |

(Continued)

*Primary Examiner* — Marcela I. Shirsat
(74) *Attorney, Agent, or Firm* — Kramer Amado, P.C.

(57) ABSTRACT

A system, comprises an implant including an outer sleeve and a head element, the outer sleeve extending longitudinally and including a channel extending therethrough, the head element including a shaft portion and a bone-engaging portion, the shaft portion received within the channel of the outer sleeve and longitudinally movable relative thereto and a clip device removably assembled with the implant to hold the outer sleeve and the head element in a desired position relative to one another, the clip device including a body extending longitudinally along with a separation portion connected to a proximal end of the body via a releasable connection to engage the proximal end of the outer sleeve and a spacer portion connected to the proximal end of the body to releasably engage a portion of the shaft portion between a proximal end of the bone-engaging portion and the distal end of the outer sleeve.

20 Claims, 4 Drawing Sheets

(51) Int. Cl.
*A61B 17/88* (2006.01)
*A61B 17/74* (2006.01)
*A61B 17/17* (2006.01)
*A61F 2/36* (2006.01)
*A61B 17/16* (2006.01)
*A61B 17/68* (2006.01)
*A61B 90/00* (2016.01)
*A61B 17/86* (2006.01)

(56) References Cited

U.S. PATENT DOCUMENTS

2004/0172035 A1* 9/2004 Parmigiani .......... A61C 8/0089
 606/80
2011/0004255 A1* 1/2011 Weiner ............... A61B 17/7291
 606/301
2011/0174117 A1* 7/2011 Franco ................. B25B 23/101
 81/44

* cited by examiner

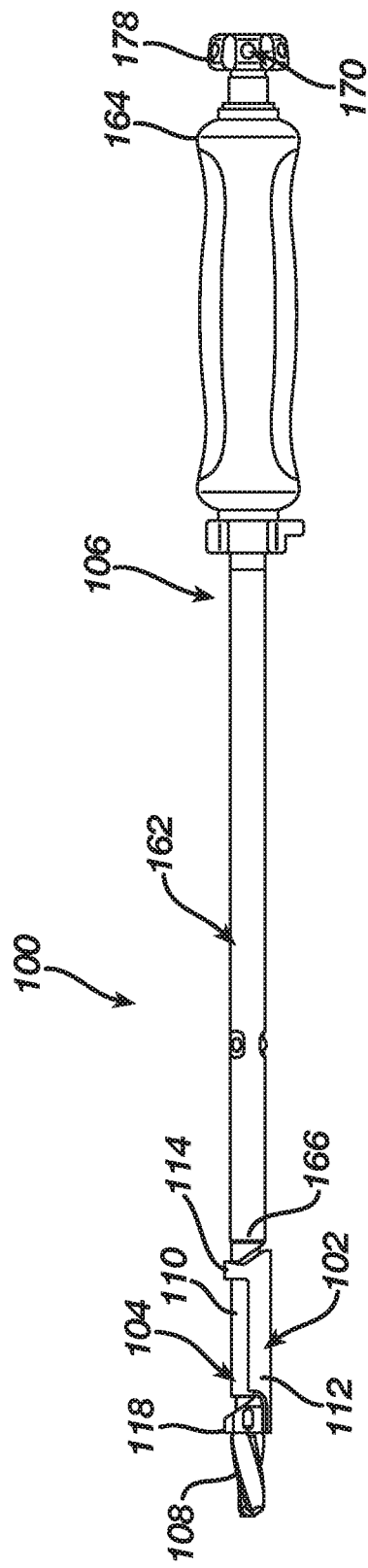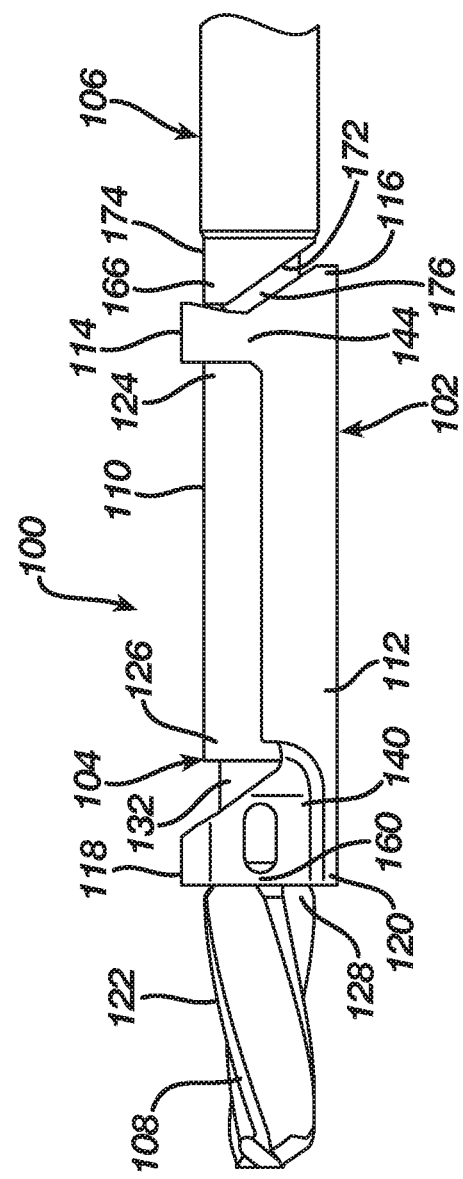

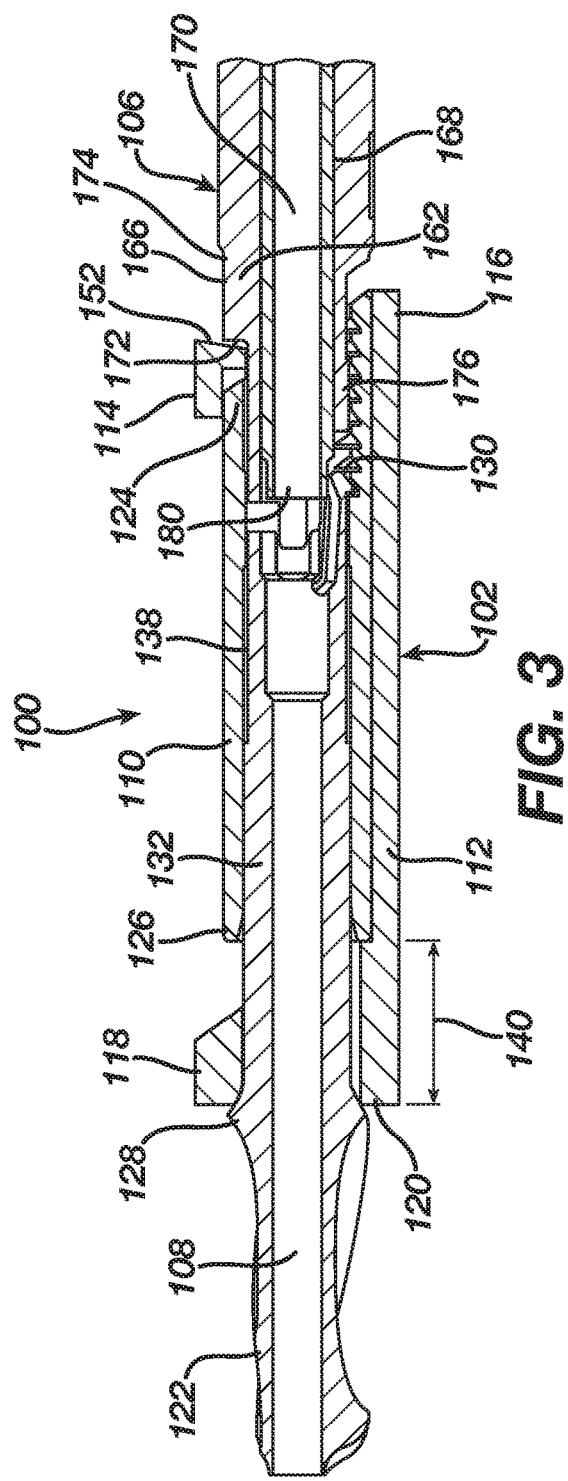
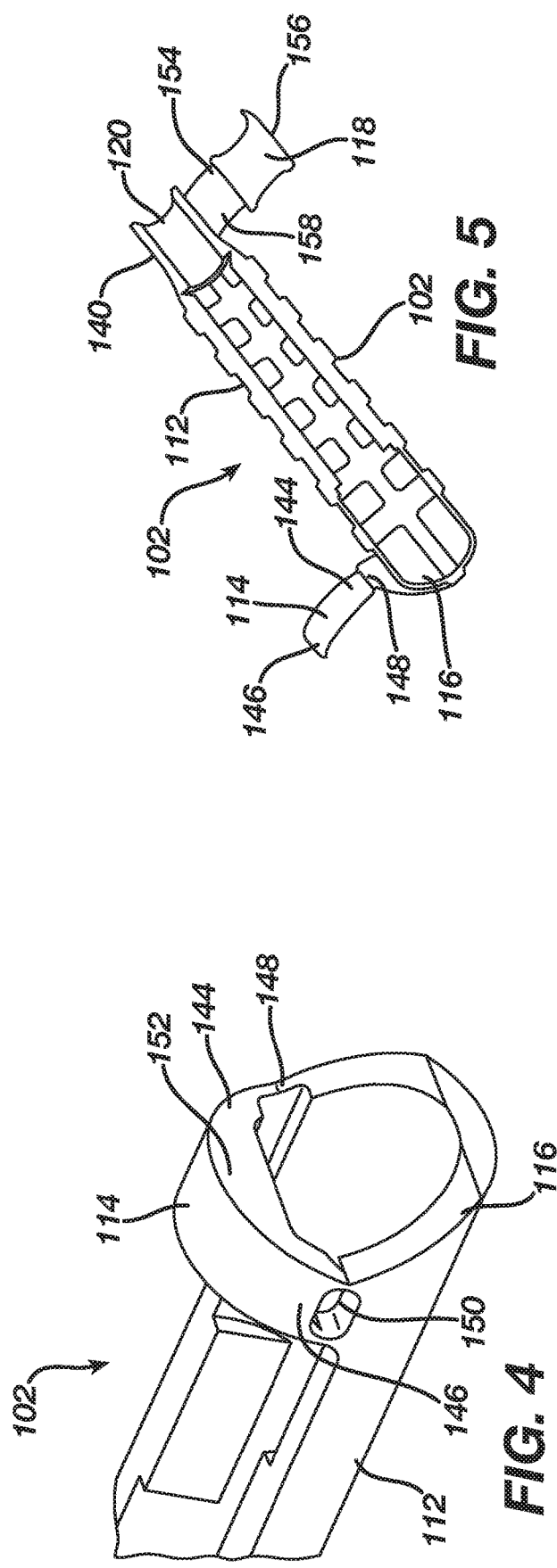

BREAK OFF SPACER CLIP FOR TROCHANTERIC FEMORAL NAIL TELESCOPING HEAD ELEMENT

BACKGROUND

Bone fractures are often treated with screws or other fixation devices inserted into the bone to stabilize portions thereof once they have been brought into corrective alignment. In particular, hip fractures (e.g., trochanteric fractures of the proximal femur) may be treated using proximal femoral nail systems including the insertion of an intramedullary nail into a medullary cavity of a long bone such as a femur and a subsequent insertion of an implant into the femoral head angled relative to the intramedullary nail (e.g., along an axis of the femoral neck). In some cases, the implant may include a telescoping femoral head component to permit compression of the bone during healing.

SUMMARY

The present invention is directed to a system for treating a bone comprising an implant including an outer sleeve and a head element, the outer sleeve extending longitudinally from a proximal end to a distal end and including a channel extending longitudinally therethrough, the head element including a shaft portion and a bone-engaging portion at a distal end of the shaft portion, the shaft portion received within the channel of the outer sleeve and longitudinally movable relative thereto and a clip device removably assembled with the implant to hold the outer sleeve and the head element in a desired position relative to one another, the clip device including a body extending longitudinally from a proximal end to a distal end along with a separation portion connected to the proximal end of the body via a releasable connection to engage the proximal end of the outer sleeve and a spacer portion connected to the proximal end of the body to releasably engage a portion of the shaft portion between a proximal end of the bone-engaging portion and the distal end of the outer sleeve, the releasable connection of the separation portion configured to disengage when subject a force exceeding a predetermined threshold value.

The present invention is also directed to a system for treating a bone, comprising an implant including an outer sleeve and a head element, the outer sleeve extending longitudinally from a proximal end to a distal end and including a channel extending longitudinally therethrough, the head element including a shaft portion and a bone-engaging portion at a distal end of the shaft portion, the shaft portion received within the channel of the outer sleeve and longitudinally movable relative thereto, a clip device removably assembled with the implant to hold the outer sleeve and the head element in a desired position relative to one another, the clip device including a body extending longitudinally from a proximal end to a distal end along with a separation portion connected to the proximal end of the body to releasably engage the proximal end of the outer sleeve and a spacer portion connected to the proximal end of the body to releasably engage a portion of the shaft portion between a proximal end of the bone-engaging portion and the distal end of the outer sleeve, and an insertion device configured to be coupled to the implant so that, when a distal end of the insertion device is inserted into the channel of the outer sleeve, a portion of the insertion device exerts a distal force on the separation portion causing a portion of the separation portion to disengage the body to release the proximal end of the outer sleeve therefrom.

BRIEF DESCRIPTION

FIG. 1 shows a longitudinal side view of a system according to an exemplary embodiment of the present invention;

FIG. 2 shows a longitudinal side view of a distal portion of the system of FIG. 1;

FIG. 3 shows a longitudinal cross-sectional view of the distal portion of the system of FIG. 1;

FIG. 4 shows a proximal portion of a clip device according to the system of FIG. 1;

FIG. 5 shows a perspective view of the clip device with first and second break elements in a broken configuration, according to the system of FIG. 1;

DETAILED DESCRIPTION

Figure 6:
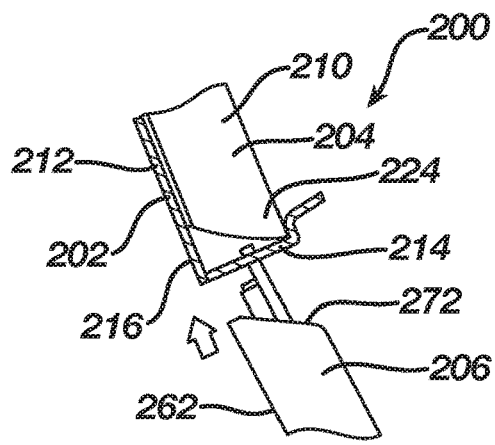
FIG. 6 shows a longitudinal side view of a portion of a system according to another exemplary embodiment of the present disclosure.

The present disclosure may be further understood with reference to the following description and the appended drawings, wherein like elements are referred to with the same reference numerals. The present embodiments relate to the treatment of a bone and, in particular, relate to the treatment of fractures of long bones such as the femur. Fractures of the femur may be treated using a proximal femur nailing system including an intramedullary nail insertable into a medullary canal of the femur and an implant insertable through the intramedullary nail and into a head of the femur along an axis of the femoral neck. The implant may include a head element which telescopes with respect to an outer sleeve. The head element may be connected to the outer sleeve via, for example, a ratchet mechanism configured to allow the implant to collapse along its length. The ratchet mechanism is configured to permit a compression of the fracture during healing while preventing medial migration of the head element toward the acetabulum. To ensure the implant is not damaged prior to insertion into the bone, the implant should be prevented from collapsing prior to implantation. If the implant collapses prior to insertion, there is a risk that the ratchet mechanism may be damaged during insertion into the bone, under the force of hammering. If the ratchet mechanism breaks, the head element may become separated from the outer sleeve, resulting in medial migration of the head element toward the acetabulum. The exemplary embodiments describe a device for holding the head element and the outer sleeve of the implant relative to one another during coupling of the implant to an insertion device. The device comprises a body configured to hold the head element and the outer sleeve in a desired position relative to one another, the body including one or more breakable portions to facilitate removal of the device after the insertion device has been coupled to the implant and prior to insertion of the implant into the bone. It will be understood by those of skill in the art that the terms proximal and distal, as used herein refer to a direction toward (proximal) and away from (distal) a user of the system described herein. It will be further understood that, although the embodiments described herein are directed to the femur, systems for treating other long bones such as the humerus may be substantially similarly constructed.

As shown in FIGS. 1-5, a system 100 comprises a clip device 102 for holding an implant 104 in a desired configuration during coupling of the implant 104 to an insertion device 106. The implant 104 is configured to be inserted through an intramedullary nail and into a head portion of a bone (e.g., femur) and may be inserted into the bone via hammer blows to a proximal end of the insertion device 106. The implant 104 includes a head element 108 and an outer sleeve 110 connected to one another via, for example, a ratchet mechanism 130 configured to allow the implant 104 to collapse along its length while preventing the implant 104 from lengthening. The clip device 102 includes a body 112 sized and shaped to extend along and about at least a portion of the implant 104 so that the implant 104 is held in a desired configuration during connection of the implant 104 to the insertion device 106. In other words, the clip device 102 holds the implant 104 so that the head element 108 and the outer sleeve 110 are fixed in a desired position relative to one another. The clip device 102 includes a first separation portion 114 connected to a proximal end 116 of the body 112 so that, when the insertion device 106 is pushed against the first separation portion 114 during connection to the implant 104, the first separation portion 114 separates (e.g., is broken) and/or deforms to facilitate removal of the clip device 102 therefrom. The clip device 102 also includes a spacing element 118 connected to a distal end 120 of the body 112. The spacing element 118 is configured to maintain a desired space between a proximal end 128 of bone-engaging element 122 of the head element 108 and a distal end 126 of the outer sleeve 110 so that the head element 108 and the outer sleeve 110 are held in the desired position relative to one another.

The implant 104 includes the head element 108 and the outer sleeve 110. The outer sleeve 110 extends longitudinally from a proximal end 124 to a distal end 126 and includes a channel 138 extending therethrough. The proximal end 124 of the outer sleeve 110 may be beveled so that, when the implant 104 is inserted through the intramedullary nail and into the head portion of the bone at an angle relative to a longitudinal axis of the intramedullary nail (e.g., parallel to an axis of the femoral neck), the proximal end 124 is flush with an exterior surface of the intramedullary nail or received within the intramedullary nail. The head element 108 includes a shaft 132 sized and shaped to be received within the channel 138 and a bone-engaging element 122 at a distal end 136 thereof. As described above, the shaft 132 of the head element 108 and the channel 138 of the outer sleeve 102 may engage one another via a ratchet mechanism 130 which permits proximal movement of the head element 108 relative to the outer sleeve 102 while preventing distal movement of the head element 108 relative to the outer sleeve 110. The bone-engaging element 122 has a cross-sectional area larger than a cross-sectional area of the shaft 132 and may have any of a variety of bone-engaging features such as, for example, threading or helical blades as would be understood by those skilled in the art.

The clip device 102 includes the body 112 extending longitudinally from a proximal end 116 to a distal end 120, the first separation portion 114 at the proximal end 116 and the spacer portion 118 at the distal end 120. The clip device 102 may be pre-assembled with the implant during manufacturing. The body 112 is sized and shaped to extend about a portion of a periphery of the outer sleeve 110. In one embodiment, the body 112 has a hemispherical cross-sectional shape. A length of the body 112 (i.e., a distance between the proximal end 116 and the distal end 120 of the body 112) may be selected to extend from the proximal end 124 of the outer sleeve 110 to the proximal end 128 of the bone-engaging element 122, when the head element 108 and the outer sleeve 110 are in the desired position relative to one another. The proximal end 116 of the body 112 may, for example, be beveled to correspond to the beveled proximal end 124 of the outer sleeve 110. A distal portion 140 of the body 112 extending between the distal end 126 of the outer sleeve 110 and the proximal end 128 of the bone-engaging element 122 may be specifically sized and shaped to extend about a portion of the shaft 132 extending therebetween.

The first separation portion 114, as shown in FIGS. 4-5, is connected to the proximal end 116 of the body 112, extending from a first end 144 connected to the body 112 via, for example, a living hinge 148 to a second end 146 connected to the body 112 via a releasable connection 150. The living hinge 148 may be formed via a thinned portion of a wall defining the body 112. As would be understood by those skilled in the art, the releasable connection 150 may be any connection configured to break, disengage or otherwise disconnect when subject to a force beyond a predetermined threshold value. The first separation portion 114 extends about a portion of the periphery of the outer sleeve 110 so that the body 112 and the first separation portion 114 together extend about the entire periphery (e.g., circumference) of the outer sleeve 110. Thus, the first separation portion 114 holds the outer sleeve 110 in a desired position relative to the body 112. In one embodiment, the first separation portion 114 extends along a curve. The first separation portion 114 also includes a proximal face 152 which extends proximally over a proximal edge of the proximal end 124 of the outer sleeve 110. The proximal face 152 may be substantially planar and configured to come into contact with a portion of the insertion device 106, as the insertion device 106 is being coupled to the implant 104. In particular, when the insertion device 106 exerts a distal force on the proximal face 152 beyond the predetermined threshold value, the releasable connection 150 is broken or disconnected so that the first separation portion 114 remains connected to the body 112 only via the living hinge 148. Alternatively, the first separation portion 114 may be deformed when the insertion device is pressed distally thereagainst so that the user may manually break or release the releasable connection 150.

The spacer portion 118 is connected to the distal end 120 of the body 112 and is sized and shaped to extend about a portion of the shaft 132 extending between the distal end 126 of the outer sleeve 110 and the proximal end 128 of the bone-engaging element 122 when the implant 104 is in the desired configuration. The spacer portion 118 and the distal portion 140 of the body 112 together may extend about an entire periphery of the shaft portion 132. The spacer portion 118, together with the distal portion 140, is configured to maintain the desired distance between the distal end 126 of the outer sleeve 110 and the proximal end 128 of the bone-engage element 122. In the embodiment shown, the spacer portion 118 may be configured as a second separation portion, extending from a first end 154 connected to the body 112 via a living hinge 158 to a second end 156 connected to the body 112 via a releasable connection 160 designed to break, disengage, or otherwise disconnect when subject to a predetermined threshold force. It will be understood by those of skill in the art, however, that the spacer portion 118 may have any of a variety of configurations so long as the spacer portion 118 is configured to be disengagable from the implant 104 when subject to a predetermined threshold force.

As described above, the first separation portion 114 may be separated as a portion of the insertion device 106 engages the outer sleeve 110 of the implant 104. Once the first separation portion 114 has been separated and the insertion device 106 has been coupled to the implant 104, as will be described in further detail below, the user may lift or angle the implant 104 relative to the longitudinal axis of the clip device 102, separating the spacer portion 118. In other words, after the first separation portion 114 has been broken, the user is able to lift the proximal end 124 of the outer sleeve 110 out of the clip device 102 (via the insertion device 106), thereby angling the implant 104 relative to the clip device 102 until the spacer portion 118 is disconnected. Upon disconnecting the releasable connection 160 of the spacer portion 118, the entire implant 104, is released from the clip device 102.

The insertion device 106 may include a blade impactor 162 configured to be connected to the outer sleeve 110 of the implant 104 and a connector screw 170 configured to be connected to the head element 108 of the implant 104. The blade impactor 162 extends from a proximal end 164 to a distal end 166 configured to be connected to the proximal end 124 of the outer sleeve 110 of the implant 104. The blade impactor 162 also includes a lumen 168 sized and shaped to rotatably house a portion of a length of the connector screw 170 therein. The distal end 166 of the blade impactor 162 may include a shoulder 172 along an exterior surface 174 thereof so that a portion 176 of the impactor 162 distal of the shoulder 172 is sized and shaped to be insertable into the channel 138 of the outer sleeve 110 while the shoulder 172 is configured to abut the proximal end 124 of the outer sleeve 110. The shoulder 172 may be beveled (e.g., angled) to correspond to the beveled proximal end 124 of the outer sleeve 110 of the implant 104.

The connector screw 170 extends through the lumen 168 of the blade impactor 162 such that the connector screw 170 is rotatable about a longitudinal axis thereof, relative to the blade impactor 162. The connector screw 170 extends from a proximal end 178 extending proximally of the proximal end 164 of the blade impactor 162 to a distal end 180 configured to engage a proximal end 133 of the shaft 132 of the head element 108. The distal end 180 is configured to non-rotatably engage the head element 108 so that, when the proximal end 178 of the connector screw 170 is hammered to insert the implant 104 into the bone, the implant 104 is moved distally into the bone as head element 108 rotates so that the blades or threads of the bone-engaging portion 132 of the head element 108 engage the bone. Once the insertion device 106 has been coupled to the implant 104, as described above, the insertion device 106 holds the head element 108 and the outer sleeve 110 in the desired position relative to one another so that the clip device 102 may be removed without fear of the head element 108 and the outer sleeve 110 inadvertently collapsing relative to one another.

As described above, the implant 104 may be preassembled with the clip device 102 with the spacer portion 118 positioned between the proximal end 128 of the bone-engaging element 122 and the distal end 126 of the outer sleeve 110 to maintain the desired distance therebetween. The first separation portion 114 extends over the proximal end 128 of the outer sleeve 110. According to an exemplary method, the implant 104 may be coupled to the insertion device 106 by inserting the distal end 166 of the blade impactor 162 into the proximal end 124 of the outer sleeve 110 until the shoulder 172 is pressed against the proximal face 152 of the first separation portion 114, breaking and/or disengaging the releasable connection 150 thereof. As described above, in another embodiment, pressing the blade impactor 162 against the first separation portion 114 may deform the first separation portion so that the releasable connection 150 may be manually broken, released or otherwise disengaged by the user.

As the blade impactor 162 is coupled to the outer sleeve 110, the distal end 180 of the connector screw 170 is also inserted into the outer sleeve 110 to non-rotatably engage the proximal end 133 of the shaft 132 of the head element 108. Upon connection of the insertion device 106 to the implant 104 and disconnection of the first separation portion 114, the proximal end 124 of the outer sleeve 110 is released from the proximal end 116 of the clip device 102 so that the user may lift the proximal end 124 of the outer sleeve 110 out of the body 112 of the clip device 102 until the implant 104 is released from the spacer portion 118. In other words, using the insertion device 106, the user may angle the implant 104 relative to the clip device 102 until the implant 104 is released from the spacer portion 118 by, for example, disengaging the releasable connection 160 of the spacer portion 118. Once the first separation portion 114 and the spacer portion 118 have both been released, the clip device 102 is entirely removable from the implant 104 so that the implant 104 may be inserted into the bone.

As shown in FIGS. 6-10, a system 200 according to another exemplary embodiment may be substantially similar to the system 100, described above, including a clip device 202 for holding an implant 204 in a desired configuration during coupling of the implant 204 to an insertion device 206. In particular, as described above, the clip device 202 holds a head element 208 and an outer sleeve 210 of the implant 204 in a desired position relative to one another so that the implant 204 does not collapse prior to insertion into a bone. The implant 204 and the insertion device 206 may be substantially similar to the implant 104 and the insertion device 106, respectively, as described above with respect to the system 100.

Figure 8:
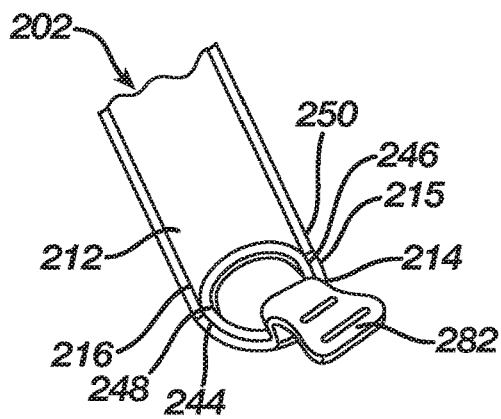
FIG. 8 shows a perspective view of a proximal portion of the clip device according to the system of FIG. 6.
Figure 9:
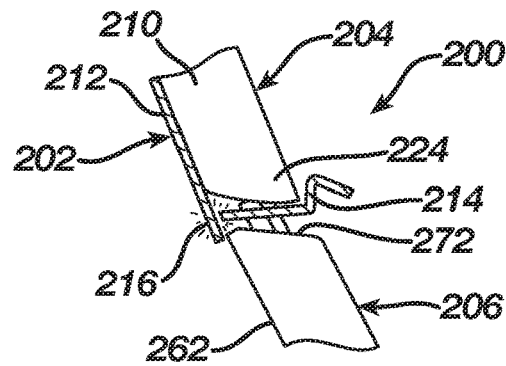
FIG. 9 shows a longitudinal side view of a portion of the system of FIG. 6, with a break portion of the clip device in a disengaged configuration.

Similarly to the clip device 102, the clip device 202 includes a body 212 extending longitudinally from a proximal end 216 to a distal end 220 along with a first separation portion 214 and a spacer portion 218. Rather than being configured to extend about a proximal portion of the outer sleeve 210, however, the first separation portion 214 is connected to the proximal end 216 of the body 212 so that, when the clip device 202 is assembled with the implant 204, the first separation portion 214 is positioned proximally of a proximal end 224 of the outer sleeve 210. The first separation portion 214, as shown in FIG. 8, includes an arched or curved portion 215 extending from a first end 244 to a second end 246, the first and second ends 244, 246 connected to the proximal end 216 via releasable connections 248, 250, respectively. The curved portion 215 may be sized and shaped so that, an outer perimeter thereof substantially corresponds to a size and shape of a blade impactor 262 of the insertion device 206. The curved portion 215 of this exemplary embodiment extends in a plane substantially perpendicular to a longitudinal axis of the body 212 so that, when a beveled shoulder 272 of a blade impactor 262 of the insertion device 206 is pressed distally thereagainst during coupling of the insertion device 206 to the implant 204, the releasable connections 248, 250 are disengaged. Once the curved portion 215 is disengaged from the body 212, the first separation portion 214 may be removed from between the insertion device 206 and the implant 204.

Figure 7:
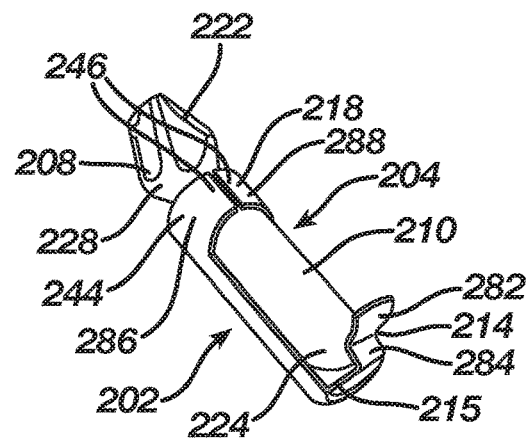
FIG. 7 shows a perspective view of a clip device assembled with an implant according to the system of FIG. 6.
Figure 10:
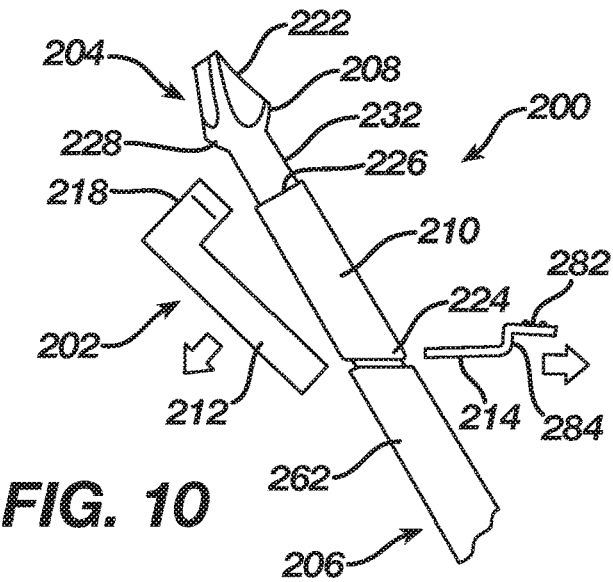
FIG. 10 shows a longitudinal side view of the system of FIG. 6 during a removal of the clip device.
Figure 11:
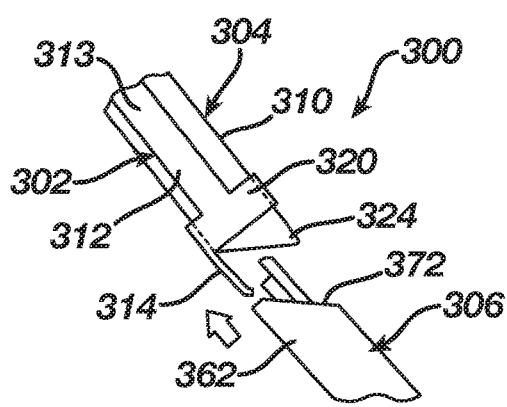
FIG. 11 shows a longitudinal side view of a portion of a system according to yet another exemplary embodiment of the present disclosure.
Figure 12:
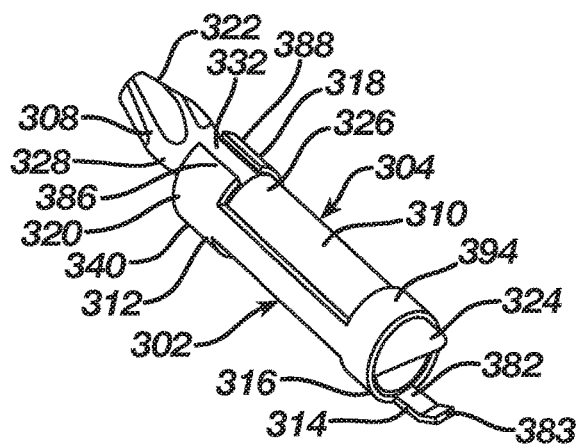
FIG. 12 shows a perspective view of a clip device assembled with an implant according to the system of FIG. 11.
Figure 13:
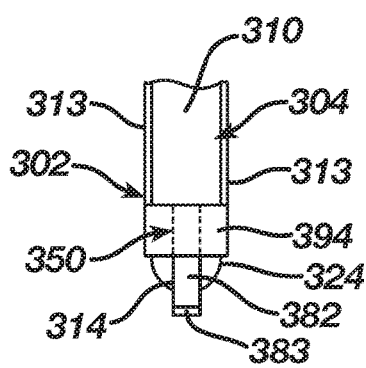
FIG. 13 shows a longitudinal side view of a proximal portion of the clip device according to the system of FIG. 11.
Figure 14:
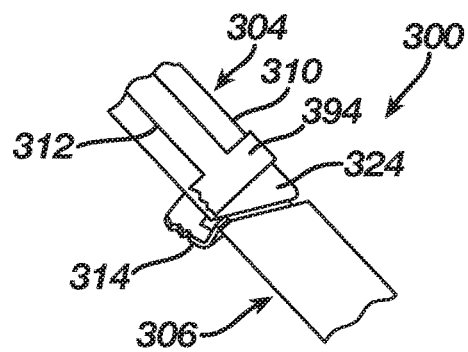
FIG. 14 shows a longitudinal side view of a portion of the system of FIG. 6, with a break portion of the clip device in a disengaged configuration.

The first separation portion 214 may further include a gripping tab 282 connected to the curved portion 215 via a connecting portion 284 which, when the clip device 202 is assembled with the implant 204, extends over a portion of the proximal end 224 of the outer sleeve 210 as shown in FIGS. 6-7. In particular, the connecting portion 284 may extend over a proximal-most portion of the outer sleeve 210 (wherein the proximal end 224 of the outer sleeve 210 is beveled), holding the proximal end 224 of the outer sleeve 210 relative to the proximal end 216 of the body 212 of the clip device 202. In one embodiment, the gripping tab 282 is connected to the proximal end 216 of the body 212 via the connecting portion 284 such that the gripping tab 282 extends along a plane different from the plane along which the curved portion 215 extends. In one embodiment, the gripping tab 282 extends substantially parallel to the curved portion 215. Once the releasable connections 248, 250 have been disengaged as described above, the first separation portion 214 may be removed from between the insertion device 206 and the implant 204 via the gripping tab 282, as shown in FIG. 10, so that the proximal end 224 of the outer sleeve 210 is releasable from the clip device 202.

The spacer portion 218 may be substantially similar to the spacer portion 118, extending about a shaft 232 of the head portion 208 of the implant 204, between a distal end 226 of the outer sleeve 210 and a proximal end 228 of a bone-engaging element 222 of the head element 208. The spacer portion 218, however, includes a first portion 286 and a second portion 288 connected to the distal end 220 of the body 212 so that, the first portion 286, the second portion 288 and a distal portion 240 of the body 212 together extend about a substantial portion of a periphery of the shaft portion 232, as shown in FIG. 7. The first and second arms 286, 288 extend from opposing sides of the distal end 220 of the body 212. Each of the first and second arms 286 extend from a first end 244 connected to the body 212 to a second end 246. Second ends 246 of the first and second arms 286, 288 are separated from one another. The first and second portions 286, 288 are biased toward an initial configuration in which the second ends 246 of the first and second arms 286, 288 are separated from one another via a distance smaller than a diameter of the shaft 232 so that the shaft 232 is prevented from being inadvertently disengaged therefrom. The first and second arms 286, 288, however, are deflectable so that, upon removal of the first separation portion 214 from the clip device 202 and engagement of the insertion device 206 with the implant 204, a force exerted on the first and second arms 286, 288 of the spacer portion 218 via, for example, angling the implant 204 relative to the body 212 by lifting the proximal end 224 of the outer sleeve 210 out of the proximal end 216 of the body 212, further separates the first and second arms 286, 288. In other words, the first and second arms 286, 288 are deflected to increase the distance between the second ends 246 thereof enough to permit the shaft 232 to be passed therethrough, thereby releasing the implant 204 from the clip device 202.

Alternatively, upon coupling the insertion device 206 to the implant 204 and removal of the separation portion 214, as described above, the clip body 212 may be manually pulled away from the implant 204 until the first and second arms 286, 288 deflect away from their biased configuration to allow the shaft portion 232 of the implant to be passed therebetween. It will be understood by those of skill in the art, that once the first separation portion 214 has been broken or otherwise disengaged, as described above, the spacer portion 218 may be disengaged or decoupled from the implant 204 in any of a number of ways via the deflectable arms 286, 288. Furthermore, as will be understood by those of skill in the art, the insertion device 206 may be coupled to the implant 204 in a manner substantially similar to the coupling of the insertion device 106 and the implant 104, as described above with respect to the system 100.

As shown in FIGS. 11-15, a system 300 according to another exemplary embodiment may be substantially similar to the systems 100, 200, described above, comprising a clip device 302 for holding an implant 304 in a desired configuration during coupling of an insertion device 306 to the implant 304. The implant 304 and the insertion device 306 are substantially similar to the implant 104 and the insertion device 206, described above with respect to the system 100.

The clip device 302 is substantially similar to the clip device 102, 202, including a body 312 extending longitudinally from a proximal end 316 to a distal end 320 along with a first separation portion 314 and a spacer portion 318. The body 312, however, may include a pair of longitudinal elements 313 extending parallel to one another between proximal ends 390 and distal ends 392 thereof. The distal ends 392 of the longitudinal elements 313 are connected to one another via a curved portion 340 sized and shaped to extend about a portion of a shaft portion 332 of a head element 308 of the implant 304 between, for example, a proximal end 328 of a bone-engaging portion 322 of the head element 308 and a distal end 326 of an outer sleeve 310 of the implant 304. Proximal ends 390 of the longitudinal elements 313 may be connected to one another via a ring-shaped portion 394 at the proximal end 316 of the body 312. The ring-shaped portion 394 may be substantially sized and shaped to extend about a proximal end 324 of the outer sleeve 310 of the implant 304. As shown in the figures, when the clip device 302 is assembled with the implant 304, the distal end 316 of the body 312 may be substantially aligned with a distal-most point of the beveled proximal end 324 of the outer sleeve 310 so that the ring-shaped portion 394 is distal of the proximal-most end of the proximal end 324. It will be understood by those of skill in the art that although the proximal and distal ends 316, 320 of the body 312 are described and shown as having a curved and/or ring shape, portions 340, 394 of the body 312 may have any of a variety of shapes so long as the portions 340 correspond to a shape of the shaft 332 and the outer sleeve 310, respectively.

The spacer portion 318 may be substantially similar to either of the spacer portions 118, 218, described above with respect to the systems 100, 200. In the embodiment shown, for example, the spacer portion 318 is substantially similar to the spacer portion 218 including deflectable first and second arms 386, 388 connected to the distal end 320 of the body 312 to maintain a desired distance between a distal end 326 of an outer sleeve 310 of the implant 304 and a proximal end 328 of a bone-engaging element 322 of a head element 308 of the implant 304. In particular, the first and second arms 386, 388 extend from the curved distal portion 340 so that together, the first and second arms 386, 388 and the distal portion 340 of the body 312 extend substantially about a periphery of the shaft portion 332.

The first separation portion 314 includes a tab 382 connected to the ring-shaped portion 394 and extending distally therefrom. The tab 382 may be connected to the ring-shaped portion 394 via a releasable connection 350 which is configured to break, separate or otherwise disengage the tab 382 from the ring-shaped portion 394 when subject to a force exceeding a predetermined threshold force. In particular, the releasable connection 350 is configured so that as the tab 382 breaks away or separates from the ring-shaped portion 394, a portion of the ring-shaped portion 394 is removed along with the tab 382, creating an opening in the ring-shaped portion 394 through which the outer sleeve 310 of the implant 304 may be removed from the clip device 302. The tab 382 may include an angled tip 383 which extends toward a central axis of the longitudinal body 312 so that, when a portion of the insertion device 306 is pushed distally thereagainst, a force is exerted on the tab 382, causing disengagement of the tab 382 from the ring-shaped portion 394. Thus, the clip device 302 is assembled with the implant 304 such that the tab 382 extends along a side of the implant 304 opposite the proximal-most point of the beveled proximal end 324 of the outer sleeve 310.

Figure 15:
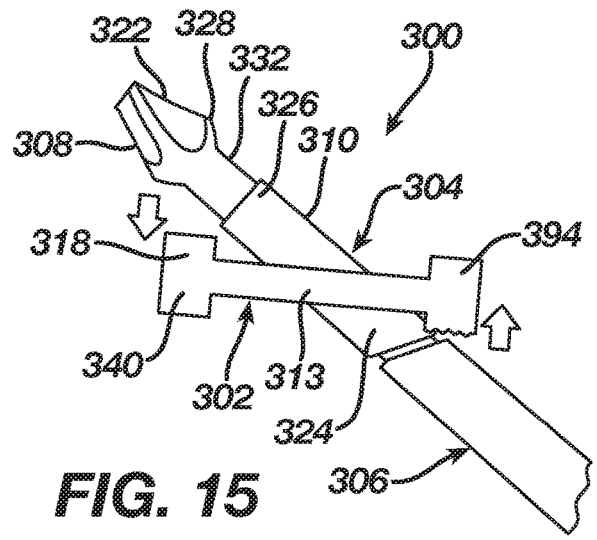
FIG. 15 shows a longitudinal side view of the system of FIG. 6 during a removal of the clip device.

During coupling of the insertion device 306 with the implant 304, a shoulder 372 of a blade impactor 362 of the insertion device 306 comes into contact with and is moved distally against the angled tip 383 of the tab 382, causing the tab 382 to break away from the ring-shaped portion 394 via the releasable connection 350. As discussed above, the releasable connection 350 is configured so that, as the tab 382 breaks away, an opening is formed in the ring-shaped portion 394. Thus, once the tab 382 has been broken or otherwise disengaged from the ring-shaped portion, the clip device 302 may be removed from the implant 304 by angling the clip device 302 relative to the implant 304, as shown in FIG. 15, so that the proximal end 324 of the outer sleeve 310 is passed through the opening. This angling of the clip device 302 relative to the implant 302 also causes the deflectable portions 386, 388 of the spacer portion 318 to deflect, allowing the shaft portion 332 of the implant 304 to be released therefrom. Once the implant 304 has been released from both the first separation portion 314 and the spacer portion 318, as described, the clip device 302 may be entirely removed from the implant 304 by drawing the implant 304 out of the clip device 302 from between the pair of longitudinal elements 313. The implant 304 is now ready to be implanted into a bone, as desired. It will be understood by those of skill in the art that the insertion device 306 may be coupled to the implant 304 in a manner substantially similarly to the insertion device and implant of the system 100.

It will be understood by those of skill in the art that modifications and variations may be made in the structure and methodology of the present invention, without departing from the spirit and scope of the invention. Thus, it is intended that the present invention cover the modifications and variations of this invention, provided that they come within the scope of the appended claims and their equivalents.

What is claimed is:

1. A system for treating a bone, comprising:
an implant including an outer sleeve and a head element, the outer sleeve extending longitudinally from a proximal end to a distal end and including a channel extending longitudinally therethrough, the head element including a shaft portion and a bone-engaging portion at a distal end of the shaft portion, the shaft portion received within the channel of the outer sleeve and longitudinally movable relative thereto; and
a clip device removably assembled with the implant to hold the outer sleeve and the head element in a desired position relative to one another, the clip device including a body extending longitudinally from a proximal end to a distal end along with a separation portion connected to the proximal end of the body via a releasable connection to engage the proximal end of the outer sleeve and a spacer portion connected to the distal end of the body to releasably engage a portion of the shaft portion between a proximal end of the bone-engaging portion and the distal end of the outer sleeve, the releasable connection of the separation portion configured to break when subject to a distal force exceeding a predetermined threshold value.

2. The system of claim 1, wherein the shaft portion and the outer sleeve are connected to one another via a ratchet mechanism permitting a proximal motion of the head element relative to the outer sleeve and preventing a distal motion of the head element relative to the outer sleeve.

3. The system of claim 1, wherein the proximal end of the outer sleeve is beveled.

4. The system of claim 3, wherein the separation portion includes a curved portion extending along a curve from a first end to a second end such that the curved portion is positioned proximally of the proximal end of the outer sleeve, the first and second ends connected to the body via the releasable connection.

5. The system of claim 1, wherein the separation portion includes a curved portion extending from a first end connected to the body via a living hinge to a second end connected to the body via the releasable connection so that the curved portion extends about the proximal end of the outer sleeve.

6. The system of claim 1, wherein the body includes a pair of longitudinal elements extending from proximal ends to distal ends, the distal ends of the longitudinal elements connected to one another via a distal portion sized and shaped to extend about a portion of a periphery of the shaft portion between the proximal end of the bone-engaging portion and the distal end of the outer sleeve, the proximal ends of the longitudinal elements connected to one another via a proximal portion sized and shaped to extend about the proximal end of the outer sleeve.

7. The system of claim 6, wherein the separation portion includes a break tab connected to the proximal portion via the releasable connection, the break tab extending proximally from the proximal portion, disengagement of the break tab from the proximal portion forming an opening in the proximal portion through which the proximal end of the outer sleeve may be removed therefrom.

8. The system of claim 7, wherein the break tab includes a tip extending toward a central axis of the clip device.

9. The system of claim 1, wherein the body of the clip device is curved to extend about a portion of the outer sleeve.

10. The system of claim 1, wherein the spacer portion includes a curved portion extending from a first end connected to the body via a living hinge to a second end connected to the body via a releasable connection, the releasable connection of the spacer portion configured to disengage when subject to a force exceeding a predetermined threshold value.

11. The system of claim 1, wherein the spacer portion includes a first deflectable arm and a second deflectable arm, the first and second deflectable arms extending from first ends connected to opposing sides of the body to second ends separated from one another by a distance smaller than a diameter of the shaft portion, the first and second deflectable arms deflectable when subject to a predetermined threshold force to increase the distance between the second ends to permit passage of the shaft portion therethrough.

12. A system for treating a bone, comprising:
an implant including an outer sleeve and a head element, the outer sleeve extending longitudinally from a proximal end to a distal end and including a channel extending longitudinally therethrough, the head element including a shaft portion and a bone-engaging portion at a distal end of the shaft portion, the shaft portion received within the channel of the outer sleeve and longitudinally movable relative thereto; and
a clip device removably assembled with the implant to hold the outer sleeve and the head element in a desired position relative to one another, the clip device including a body extending longitudinally from a proximal end to a distal end along with a separation portion connected to the proximal end of the body via a releasable connection to engage the proximal end of the outer sleeve and a spacer portion connected to the distal end of the body to releasably engage a portion of the shaft portion between a proximal end of the bone-engaging portion and the distal end of the outer sleeve, the releasable connection of the separation portion configured to disengage when subject to a force exceeding a predetermined threshold value;
wherein the separation portion includes:
a curved portion positioned proximally of the proximal end of the outer sleeve, connected to the body via the releasable connection; and
a gripping tab connected to the curved portion via a connection portion extending over a proximal-most point of the outer sleeve so that, when the releasable connection is disengaged, the separation portion is removable from the clip device via the gripping tab.

13. A system for treating a bone, comprising:
an implant including an outer sleeve and a head element, the outer sleeve extending longitudinally from a proximal end to a distal end and including a channel extending longitudinally therethrough, the head element including a shaft portion and a bone-engaging portion at a distal end of the shaft portion, the shaft portion received within the channel of the outer sleeve and longitudinally movable relative thereto;
a clip device removably assembled with the implant to hold the outer sleeve and the head element in a desired position relative to one another, the clip device including a body extending longitudinally from a proximal end to a distal end along with a separation portion connected to the proximal end of the body to releasably engage the proximal end of the outer sleeve and a spacer portion connected to the distal end of the body to releasably engage a portion of the shaft portion between a proximal end of the bone-engaging portion and the distal end of the outer sleeve; and
an insertion device configured to be coupled to the implant so that, when a distal end of the insertion device is inserted into the channel of the outer sleeve, a portion of the insertion device exerts a distal force on the separation portion causing a portion of the separation portion to disengage the body to release the proximal end of the outer sleeve therefrom.

14. The system of claim 13, wherein the separation portion includes a curved portion extending from a first end connected to the body via a living hinge to a second end connected to the body via a releasable connection so that the curved portion extends about the proximal end of the outer sleeve.

15. The system of claim 13, wherein the separation portion includes a curved portion extending along a curve from a first end to a second end such that the curved portion is positioned proximally of the proximal end of the outer sleeve, the first and second ends connected to the body via a releasable connection, a gripping tab connected to the curved portion via a connection portion extending over a proximal-most point of the outer sleeve so that, when the releasable connection is disengaged, the separation portion is removable from the clip device via the gripping tab.

16. The system of claim 13, wherein the body includes a pair of longitudinal elements extending from proximal ends to distal ends, the distal ends of the longitudinal elements connected to one another via a distal portion sized and shaped to extend about a portion of a periphery of the shaft portion between the proximal end of the bone-engaging portion and the distal end of the outer sleeve, the proximal ends of the longitudinal elements connected to one another via a proximal portion sized and shaped to extend about the proximal end of the outer sleeve.

17. The system of claim 16, wherein the separation portion includes a break tab connected to the proximal portion via the releasable connection, the break tab extending proximally from the proximal portion, disengagement of the break tab from the proximal portion forming an opening in the proximal portion through which the proximal end of the outer sleeve may be removed therefrom.

18. The system of claim 17, wherein the break tab includes a tip extending toward a central axis of the clip device.

19. The system of claim 13, wherein the spacer portion includes a curved portion extending from a first end connected to the body via a living hinge to a second end connected to the body via a releasable connection, the releasable connection of the spacer portion configured to disengage when subject to a force exceeding a predetermined threshold value.

20. The system of claim 13, wherein the spacer portion includes a first deflectable arm and a second deflectable arm, the first and second deflectable arms extending from first ends connected to opposing sides of the body to second ends separated from one another by a distance smaller than a diameter of the shaft portion, the first and second deflectable arms deflectable when subject to a predetermined threshold force to increase the distance between the second ends to permit passage of the shaft portion therethrough.

* * * * *